United States Patent [19]

Kohsaka et al.

[11] Patent Number: 4,522,817

[45] Date of Patent: Jun. 11, 1985

[54] PHOSPHORAMIDOTHIONATES AND FUNGICIDAL USE

[75] Inventors: Hideo Kohsaka, Takarazuka; Mitsuru Sasaki, Toyonaka; Yukio Ishiguri, Takarazuka, all of Japan

[73] Assignee: Sumitomo Chemical Company, Limited, Osaka, Japan

[21] Appl. No.: 475,166

[22] Filed: Mar. 14, 1983

[30] Foreign Application Priority Data

Mar. 15, 1982 [JP] Japan .................................. 57-41210
Mar. 16, 1982 [JP] Japan .................................. 57-42280
Oct. 5, 1982 [JP] Japan .................................. 57-175567

[51] Int. Cl.³ .................... A01N 57/30; A01N 57/32; C07F 9/24
[52] U.S. Cl. ...................... 514/95; 260/940; 260/948; 260/950; 260/951; 260/954; 549/5; 549/6; 549/218; 514/99; 514/112; 514/127; 514/129; 514/128; 514/132
[58] Field of Search ............... 260/940, 948, 950, 951, 260/954, 973, 984; 549/5, 6, 218; 424/202, 203, 210, 216, 217, 218

[56] References Cited

U.S. PATENT DOCUMENTS 3,773,859 11/1973 Schrader et al. ............... 260/984 X
3,917,753 11/1975 Satomi et al. ........................ 260/954
3,936,433 2/1976 Satomi et al. ........................ 260/954
3,943,203 3/1976 Satomi et al. ........................ 260/954
3,989,502 11/1976 Nishiyama et al. ..................... 71/78

FOREIGN PATENT DOCUMENTS 294072 12/1966 Australia .
2107999 5/1972 France .
2210614 7/1974 France .
80460 6/1973 Japan .
183743 11/1966 U.S.S.R. .

OTHER PUBLICATIONS

Nishiyama et al., Chemical Abstracts, vol. 83, (1975), 159155q.

Primary Examiner—Richard L. Raymond
Attorney, Agent, or Firm—Birch, Stewart, Kolasch & Birch

[57] ABSTRACT

A fungicidal composition which comprises as an active ingredient a fungicidally effective amount of a phosphoramidothionate of the formula:

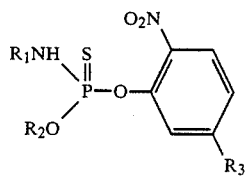

wherein $R_1$ is a lower alkyl group, a lower alkenyl group, a lower alkynyl group, a lower cycloalkyl group, a lower cycloalkyl(lower)alkyl group, a halogen atom-substituted lower alkyl group, a lower alkoxy(lower)alkyl group, a di(lower)alkoxy(lower)alkyl group, a cyano group-substituted lower alkyl group, a lower alkylthio(lower)alkyl group, a lower dioxothiacycloalkyl group, a lower thiacycloalkyl group, a lower oxacycloalkyl group, a furanyl(lower)alkyl group or a thiophenyl(lower)alkyl group, $R_2$ is a lower alkyl group and $R_3$ is a lower alkyl group or a lower alkoxy group, and an inert carrier or diluent.

10 Claims, No Drawings

PHOSPHORAMIDOTHIONATES AND FUNGICIDAL USE

The present invention relates to a fungicidal composition which comprises a fungicidally effective amount of at least one phosphoramidothionate as an active ingredient(s), and an inert carrier or diluent.

The said phosphoramidothionates are representable by the formula:

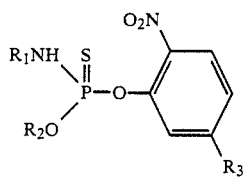

wherein $R_1$ is a lower alkyl group, a lower alkenyl group, a lower alkynyl group, a lower cycloalkyl group, a lower cycloalkyl(lower)alkyl group, a halogen atom-substituted lower alkyl group, a lower alkoxy(lower)alkyl group, a di(lower)alkoxy(lower)alkyl group, a cyano group-substituted lower alkyl group, a lower alkylthio(lower)alkyl group, a lower dioxothiacycloalkyl group, a lower thiacycloalkyl group, a lower oxacycloalkyl group, a furanyl(lower)alkyl group or a thiophenyl(lower)alkyl group, $R_2$ is a lower alkyl group and $R_3$ is a lower alkyl group or a lower alkoxy group.

In the above significances, the term "lower" is intended to mean not more than 8 carbon atoms and the term "halogen" is intended to mean chlorine, bromine, fluorine and iodine, inclusively. Preferred $R_1$ substituents are a $C_1$–$C_5$ alkyl group, a $C_3$–$C_4$ alkenyl group, a $C_3$ alkynyl group, a $C_5$–$C_6$ cycloalkyl group, a $C_3$ cycloalkyl($C_2$)alkyl group, a halo($C_2$–$C_3$)alkyl group, a $C_1$–$C_2$ alkoxy($C_2$–$C_4$)alkyl group, a di($C_1$–$C_2$)alkoxy($C_2$–$C_3$)alkyl group, a cyano($C_1$–$C_3$)alkyl group, a $C_1$ alkylthio($C_2$–$C_3$)alkyl group, a 1,1-dioxotetrahydrothiophen-3-yl group, a tetrahydrothiopyran-4-yl group, a tetrahydropyran-4-yl group, a 1-(furan-2-yl)ethyl group or a 1-(thiophenyl)ethyl group. Preferred $R_2$ substituents are a $C_1$–$C_4$ alkyl groups, and preferred $R_3$ substituents a $C_1$–$C_4$ alkyl group or a $C_1$–$C_2$ alkoxy group.

Some phosphoramidothionates of the formula (I) are disclosed in U.S. Pat. Nos. 3,943,203, 3,936,433 and 3,989,502 and Japanese Patent Publn. (unexamined) No. 44436/1973. However, these literatures do not disclose that they are useful as fungicides. Australian Pat. No. 294,072 discloses that some kinds of phosphoramidothionates, e.g. O-ethyl O-4-nitrophenyl N-allyl phosphoramidothionates, are usable as fungicides. Also, U.S.S.R. Pat. No. 183,743 discloses O-ethyl O-(3-methyl-4-nitrophenyl) N-sec-butyl phosphoramidothionate. However, the fungicidal potency of these compounds is not satisfactory.

The phosphoramidothionates (I) exhibit not only a preventive effect but also a curative effect against plant diseases such as late blight and downy mildew caused by infection of phytopathogenic fungi belonging to Phycomycetes. They also exhibit a systemic effect against above mentioned plant diseases. Thus, they are useful as fungicides.

Examples of phytopathogenic fungi belonging to Phycomycetes, against which the phosphoramidothionates (I) can exert their fungicidal activity, are as follows: *Peronospora brassicae* on vegetables and radish, *Peronospora spinaciae* on spinach, *Peronospora tabacina* on tobacco, *Pseudoperonospora cubensis* on cucumber, *Plasmopara viticola* on grape, *Plasmopara nivea* on Umbelliferae plants, *Phytophthora cactorum* on apple, strawberry and carrot, *Phytophthora capsici* on tomato and cucumber, *Phytophthora cinnamomi* on pineapple, *Phytophthora infestans* on potato, tomato and eggplant, *Phytophthora nicotianae* var. *nicotianae* on tobacco, kidney bean and onion, *Pythium aphanidermatum* on cucumber, *Pythium* sp. on spinach, *Pythium* sp. on wheat, *Pythium debaryanum* on tobacco, Pythium rot (i.e., *P. aphanidermatum*, *P. debaryanum*, *P. irregulare*, *P. myriotylum*, *P. ultimum*) on soybean and so forth.

Accordingly, the phosphoramidothionates (I) can be used as active ingredients in fungicidal compositions which can be applied to plowed fields, orchards, tea-field, mulberry-field, meadow, lawn and so on.

The phosphoramidothionates (I) may be produced according to the methods as disclosed in the said literatures. For example, they are produced by the reaction of a phosphoramidochloridothionate of the formula:

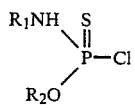

wherein $R_1$ and $R_2$ are each as defined above with a 0.9–1.1 equimolar amount of a nitrophenol of the formula:

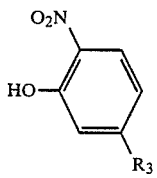

wherein $R_3$ is as defined above in a solvent in the presence of a 0.9–1.1 equimolar amount of a hydrogen halide removing agent per 1 mole of the phosphoramidochloridothionate (II) at a temperature of 20° to 120° C. for a period of 1 to 5 hours, or by the reaction of a phosphorochloridothionate of the formula:

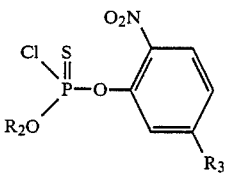

wherein $R_2$ and $R_3$ are each as defined above with a 1.0–1.2 equimolar amount of an amine of the formula:

wherein $R_1$ is as defined above in a solvent in the presence of a 1.0–2.2 equimolar amount of a hydrogen halide removing agent per 1 mole of the phosphorochloridothionate (IV) at a temperature of 0° to 50° C. for a period of 1 to 5 hours.

Examples of the solvent are an aromatic hydrocarbon (e.g. benzene, toluene, xylene), a halogenated hydrocarbon (e.g. chloroform, carbon tetrachloride, dichloroethane, chlorobenzene, dichlorobenzene), an ether (e.g. diethyl ether, diisopropyl ether, dioxane, tetrahydrofuran, diethyleneglycol dimethyl ether), a ketone (e.g. acetone, methylethylketone, cyclohexanone), a nitro compound (e.g. nitroethane, nitrobenzene), a nitrile (e.g. acetonitrile), a tertiary amine (e.g. pyridine, triethylamine, N,N-diethylaniline, tributylamine, N-methylmorpholine), an acid amide (e.g. N,N-dimethylformamide, N,N-dimethylacetamide), water and the mixture thereof.

Examples of the hydrogen halide removing agent are an organic base (e.g. pyridine, triethylamine, N,N-diethylaniline) and an inorganic base (e.g. sodium hydroxide, potassium hydroxide, sodium carbonate, potassium carbonate).

After completion of the reaction, the reaction product may be isolated by an ordinary separation procedure and, if necessary, purified by a conventional purification procedure such as chromatography, distillation or recrystallization.

Some typical examples of the production of the phosphoramidothionates (I) are shown in the following Examples.

EXAMPLE 1

5-Methoxy-2-nitrophenol (1.69 g; 0.01 mole) was dissolved in acetonitrile (25 ml), and anhydrous potassium carbonate powder (1.40 g) was added thereto. The mixture was stirred at 50°–60° C. for 30 minutes. Then, O-ethyl N-sec-butyl phosphoramidochloridothionate (2.15 g; 0.01 mole) was added dropwise at the same temperature to the mixture, which was refluxed for 4 hours with stirring. After the inorganic salt was filtered off, the solvent was evaporated. The residue was dissolved in toluene and washed with dilute hydrochloric acid, an aqueous solution of sodium hydroxide and water in order. After being dried over anhydrous sodium sulfate, toluene was evaporated, followed by purification with silica gel column chromatography to obtain 2.51 g of O-ethyl O-(5-methoxy-2-nitrophenyl) N-sec-butyl phosphoramidothionate (Compound No. 33). Yield, 72.1%; $n_D^{26.0}$, 1.5353.

EXAMPLE 2

O-Ethyl O-(5-methoxy-2-nitrophenyl)phosphorochloridothionate (6.23 g; 0.02 mole) was dissolved in toluene. While keeping this solution at 0° C., n-butylamine (1.46 g; 0.02 mole) and successively triethylamine (2.02 g; 0.02 mole) were added dropwise thereto. After the addition was completed, the mixture was stirred at room temperature for 3 hours. Then, it was washed with dilute hydrochloric acid and water. After being dried over anhydrous sodium sulfate, toluene was evaporated to obtain 6.27 g of O-ethyl O-(5-methoxy-2-nitrophenyl) N-n-butyl phosphoramidothionate (Compound No. 28). Yield, 90.1%; $n_D^{24.5}$, 1.5354.

EXAMPLE 3

5-Methoxy-2-nitrophenol (3.38 g; 0.02 mole) was dissolved in acetonitrile (50 ml), and anhydrous potassium carbonate (2.76 g; 0.02 mole) was added to the solution and stirred at 50°–60° C. for 30 minutes. Then, at the same temperature, O-methyl N-(3-methoxypropyl)phosphoramidochloridothionate (4.35 g; 0.02 mole) was added dropwise to the mixture, which was then refluxed with stirring. After the inorganic salt was filtered off, the solvent was evaporated. The residue was dissolved in toluene, and the resultant solution was washed with dilute hydrochloric acid, an aqueous solution of sodium hydroxide and water. After being dried over anhydrous sodium sulfate, toluene was evaporated. The residue was purified by silica gel column chromatography to obtain 4.90 g of O-methyl O-(5-methoxy-2-nitrophenyl) N-(3-methoxypropyl)phosphoramidothionate (Compound No. 58). Yield, 70%; $n^{24}$, 1.5425.

EXAMPLE 4

O-Ethyl O-(5-methoxy-2-nitrophenyl)phosphorochloridothionate (12.46 g; 0.04 mole) was dissolved in toluene (100 ml). 2-Methoxyethylamine (3.00 g; 0.04 mole) and successively triethylamine (4.05 g; 0.04 mole) were added dropwise thereto at 0° C. After completion of the addition, the resultant mixture was stirred at room temperature for 3 hours. Then, it was washed with dilute hydrochloric acid and water and dried over anhydrous magnesium sulfate. The drying agent was filtered off, and toluene was evaporated to obtain 13.72 g of O-ethyl O-(5-methoxy-2-nitrophenyl) N-(2-methoxyethyl)phosphoramidothionate (Compound No. 49). Yield, 98%; $n_D^{22.5}$, 1.5456.

EXAMPLE 5

5-Methoxy-2-nitrophenol (3.38 g; 0.02 mole) was dissolved in acetonitrile (50 ml), and anhydrous potassium carbonate powder (2.76 g; 0.02 mole) was added thereto. The mixture was stirred at 50°–60° C. for 30 minutes, followed by dropwise addition of O-ethyl N-1-(methoxymethyl)ethyl phosphoramidochloridothionate (4.63 g; 0.02 mole). The resultant mixture was refluxed with stirring for 4 hours, and after the inorganic salt was filtered off, acetonitrile was evaporated. The residue was dissolved in toluene, and the resultant mixture was washed with dilute hydrochloric acid, an aqueous solution of sodium hydroxide and water in order. Then, it was dried over anhydrous magnesium sulfate. The drying agent was filtered off, and toluene was evaporated. The residue was purified by silica gel column chromatography to obtain 5.10 g of O-ethyl O-(5-methoxy-2-nitrophenyl) N-1-(methoxymethyl)ethyl phosphoramidothionate (Compound No. 54). Yield, 70.1%; $n_D^{27.5}$, 1.5445.

Examples of the phosphoramidothionate (I) produced in the similar manner are shown in Table 1.

TABLE 1

$$\text{(I)} \quad R_1NH-\underset{\underset{OR_2}{|}}{\overset{S}{\overset{\|}{P}}}-O-\text{C}_6\text{H}_3(\text{o-}NO_2)(\text{R}_3)$$

| Compound No. | $R_1$ | $R_2$ | $R_3$ | Physical constant |
|---|---|---|---|---|
| 1 | $C_2H_5$ | $C_2H_5$ | $CH_3$ | M.P. 63–64° C. |
| 2 | n-$C_3H_7$ | $C_2H_5$ | $CH_3$ | $n_D^{27}$ 1.5503 |
| 3 | sec-$C_4H_9$ | $CH_3$ | $CH_3$ | $n_D^{22}$ 1.5465 |
| 4 | iso-$C_3H_7$ | $C_2H_5$ | $CH_3$ | $n_D^{20}$ 1.5256 |
| 5 | $CH_3$ | $CH_3$ | $CH_3$ | $n_D^{21}$ 1.5675 |
| 6 | sec-$C_4H_9$ | $C_2H_5$ | $CH_3$ | $n_D^{20}$ 1.5340 |
| 7 | sec-$C_4H_9$ | $C_2H_5$ | $C_2H_5$ | $n_D^{20}$ 1.5325 |
| 8 | sec-$C_4H_9$ | $C_2H_5$ | iso-$C_3H_7$ | $n_D^{20}$ 1.5280 |
| 9 | sec-$C_4H_9$ | $C_2H_5$ | tert-$C_4H_9$ | $n_D^{18}$ 1.5260 |
| 10 | $(C_2H_5)_2CH$ | $C_2H_5$ | $CH_3$ | $n_D^{21}$ 1.5720 |
| 11 | cyclopentyl-H | $C_2H_5$ | $CH_3$ | $n_D^{20}$ 1.5651 |
| 12 | cyclohexyl-H | $C_2H_5$ | $CH_3$ | $n_D^{20.5}$ 1.5490 |
| 13 | n-$C_4H_9$ | $C_2H_5$ | $CH_3$ | $n_D^{19}$ 1.5381 |
| 14 | iso-$C_4H_9$ | $C_2H_5$ | $CH_3$ | $n_D^{21.5}$ 1.5315 |
| 15 | $CH_2=CHCH_2-$ | $C_2H_5$ | $CH_3$ | $n_D^{22.5}$ 1.5530 |
| 16 | iso-$C_3H_7$ | iso-$C_3H_7$ | $CH_3$ | $n_D^{22}$ 1.5288 |
| 17 | iso-$C_3H_7$ | n-$C_3H_7$ | $CH_3$ | $n_D^{21}$ 1.5325 |
| 18 | iso-$C_3H_7$ | n-$C_4H_9$ | $CH_3$ | $n_D^{22}$ 1.5269 |
| 19 | n-$C_3H_7$ | $CH_3$ | $CH_3$ | $n_D^{22}$ 1.5448 |
| 20 | $C_2H_5$ | $CH_3$ | $CH_3$ | $n_D^{24}$ 1.5554 |
| 21 | $CH_2=CHCH_2-$ | $CH_3$ | $CH_3$ | $n_D^{30}$ 1.5569 |
| 22 | n-$C_4H_9$ | $CH_3$ | $CH_3$ | $n_D^{22}$ 1.5470 |
| 23 | iso-$C_4H_9$ | $CH_3$ | $CH_3$ | $n_D^{22}$ 1.5455 |
| 24 | $CH_3$ | $C_2H_5$ | $CH_3$ | M.P. 68.5–70.5° C. |
| 25 | sec-$C_4H_9$ | $C_2H_5$ | $OC_2H_5$ | $n_D^{26}$ 1.5337; M.P. 65–66° C. |
| 26 | iso-$C_4H_9$ | $C_2H_5$ | $OCH_3$ | $n_D^{23.5}$ 1.5430 |
| 27 | sec-$C_4H_9$ | $CH_3$ | $OCH_3$ | $n_D^{24}$ 1.5570 |
| 28 | n-$C_4H_9$ | $C_2H_5$ | $OCH_3$ | $n_D^{24.5}$ 1.5354 |
| 29 | n-$C_3H_7$ | $C_2H_5$ | $OCH_3$ | $n_D^{24}$ 1.5429 |
| 30 | iso-$C_3H_7$ | $C_2H_5$ | $OCH_3$ | $n_D^{32}$ 1.5380 |
| 31 | $C_2H_5$ | $C_2H_5$ | $OCH_3$ | $n_D^{24.5}$ 1.5539 |
| 32 | $CH_3$ | $C_2H_5$ | $OCH_3$ | $n_D^{23.5}$ 1.5675 |
| 33 | sec-$C_4H_9$ | $C_2H_5$ | $OCH_3$ | $n_D^{26.0}$ 1.5353 |
| 34 | iso-$C_3H_7$ | n-$C_3H_7$ | $OCH_3$ | $n_D^{23}$ 1.5458 |
| 35 | sec-$C_4H_9$ | n-$C_3H_7$ | $OCH_3$ | $n_D^{23}$ 1.5239 |
| 36 | cyclopentyl-H | $C_2H_5$ | $OCH_3$ | $n_D^{23}$ 1.5600 |
| 37 | cyclohexyl-H | $C_2H_5$ | $OCH_3$ | $n_D^{22.5}$ 1.5528 |
| 38 | $CH_2=CHCH_2-$ | $C_2H_5$ | $OCH_3$ | $n_D^{22.5}$ 1.5530 |
| 39 | $(C_2H_5)_2CH-$ | $C_2H_5$ | $OCH_3$ | $n_D^{22.5}$ 1.5449 |
| 40 | iso-$C_3H_7$ | n-$C_4H_9$ | $OCH_3$ | $n_D^{23}$ 1.5449 |
| 41 | $C_2H_5$ | n-$C_4H_9$ | $OCH_3$ | $n_D^{23}$ 1.5545 |
| 42 | $(CH_3)_2CH(CH_3)CH-$ | $C_2H_5$ | $OCH_3$ | $n_D^{22.5}$ 1.5279 |
| 43 | $CH_2=CH-CH(CH_3)-CH_2-$ | $C_2H_5$ | $OCH_3$ | $n_D^{21.5}$ 1.5591 |
| 44 | n-$C_4H_9$ | $CH_3$ | $OCH_3$ | $n_D^{21.5}$ 1.5595 |
| 45 | n-$C_3H_7$ | $CH_3$ | $OCH_3$ | $n_D^{21.5}$ 1.5546 |

TABLE 1-continued $$\text{(I)} \quad \begin{array}{c} R_1NH \\ \diagdown \\ R_2O \end{array} \!\!\! \overset{\overset{\displaystyle S}{\|}}{P} \!\!-\! O \!-\! \underset{R_3}{\underset{|}{\bigcirc}}\!\!\!-\!\! NO_2$$

| Compound No. | $R_1$ | $R_2$ | $R_3$ | Physical constant |
|---|---|---|---|---|
| 46 | iso-$C_3H_7$ | $CH_3$ | $OCH_3$ | M.P. 60–62° C. |
| 47 | sec-$C_4H_9$ | iso-$C_3H_7$ | $OCH_3$ | $n_D^{20.0}$ 1.5359 |
| 48 | iso-$C_3H_7$ | iso-$C_3H_7$ | $OCH_3$ | $n_D^{20.0}$ 1.5365 |
| 49 | $CH_3O(CH_2)_2$ | $C_2H_5$ | $OCH_3$ | $n_D^{22.5}$ 1.5456 |
| 50 | $CH_3OCH_2\!\!-\!\!\underset{C_2H_5}{\overset{}{CH\!-}}$ | $C_2H_5$ | $OCH_3$ | $n_D^{20.0}$ 1.5289 |
| 51 | $CH_3O(CH_2)_3$ | $C_2H_5$ | $OCH_3$ | $n_D^{20.0}$ 1.5528 |
| 52 | $C_2H_5O(CH_2)_2$ | $C_2H_5$ | $OCH_3$ | $n_D^{22.0}$ 1.5471 |
| 53 | $C_2H_5O(CH_2)_3$ | $C_2H_5$ | $OCH_3$ | $n_D^{25.5}$ 1.5404 |
| 54 | $CH_3OCH_2\!\!-\!\!\overset{\overset{\displaystyle CH_3}{\|}}{CH\!-}$ | $C_2H_5$ | $OCH_3$ | $n_D^{27.5}$ 1.5445 |
| 55 | $CH_3O(CH_2)_2\!\!-\!\!\overset{\overset{\displaystyle CH_3}{\|}}{CH\!-}$ | $C_2H_5$ | $OCH_3$ | $n_D^{27.5}$ 1.5400 |
| 56 | $CH_3O(CH_2)_2$ | $CH_3$ | $OCH_3$ | $n_D^{20}$ 1.5570 |
| 57 | $CH_3OCH_2\!\!-\!\!\underset{C_2H_5}{\overset{}{CH\!-}}$ | $CH_3$ | $OCH_3$ | $n_D^{25}$ 1.5505 |
| 58 | $CH_3O(CH_2)_3$ | $CH_3$ | $OCH_3$ | $n_D^{24}$ 1.5425 |
| 59 | $C_2H_5O(CH_2)_2$ | $CH_3$ | $OCH_3$ | $n_D^{23}$ 1.5482 |
| 60 | $C_2H_5O(CH_2)_3$ | $CH_3$ | $OCH_3$ | $n_D^{23}$ 1.5430 |
| 61 | $CH_3OCH_2\overset{\overset{\displaystyle CH_3}{\|}}{CH\!-}$ | $CH_3$ | $OCH_3$ | $n_D^{24}$ 1.5434 |
| 62 | $CH_3O(CH_2)_2\overset{\overset{\displaystyle CH_3}{\|}}{CH\!-}$ | $CH_3$ | $OCH_3$ | $n_D^{21.5}$ 1.5437 |
| 63 | $(CH_3O)_2CHCH_2$ | $C_2H_5$ | $OCH_3$ | $n_D^{21.5}$ 1.5409 |
| 64 | $(C_2H_5O)_2CHCH_2$ | $C_2H_5$ | $OCH_3$ | $n_D^{24.0}$ 1.5240 |
| 65 | $(CH_3OCH_2)_2CH\!\!-$ | $C_2H_5$ | $OCH_3$ | M.P. 38–40° C. |
| 66 | $(CH_3O)_2CH\overset{\overset{\displaystyle CH_3}{\|}}{CH\!-}$ | $C_2H_5$ | $OCH_3$ | $n_D^{24.5}$ 1.5405 |
| 67 | $\triangleright\!\!-\!\!\overset{\overset{\displaystyle CH_3}{\|}}{CH\!-}$ | $C_2H_5$ | $OCH_3$ | $n_D^{23.5}$ 1.5550 |
| 68 | $n\text{-}C_3H_7\overset{\overset{\displaystyle CH_3}{\|}}{CH\!-}$ | $C_2H_5$ | $OCH_3$ | $n_D^{26.5}$ 1.5430 |
| 69 | $HC\!\!\equiv\!\!CCH_2\!-$ | $C_2H_5$ | $OCH_3$ | $n_D^{20}$ 1.5733 |
| 70 | $\underset{S}{\langle\!\!\!\!\!\!\diagup\!\!\!\!\!\!\rangle}\!\!-\!\!\overset{\overset{\displaystyle CH_3}{\|}}{CH\!-}$ | $C_2H_5$ | $OCH_3$ | $n_D^{21.0}$ 1.5880 |
| 71 | $NCCH_2\!-$ | $C_2H_5$ | $OCH_3$ | $n_D^{21.5}$ 1.5715 |

TABLE 1-continued $$\text{(I)}$$

Structure: $R_1NH$ and $R_2O$ groups attached to $P(=S)$, which is bonded via $-O-$ to a benzene ring bearing $O_2N$ (ortho) and $R_3$ (para).

| Compound No. | $R_1$ | $R_2$ | $R_3$ | Physical constant |
|---|---|---|---|---|
| 72 | 2-(1-methyl)furyl — $CH(CH_3)$— attached to furan | $C_2H_5$ | $OCH_3$ | $n_D^{26.0}$ 1.5630 |
| 73 | $NCCH_2CH(CH_3)$— | $C_2H_5$ | $CH_3$ | $n_D^{24.5}$ 1.5450 |
| 74 | $NCCH_2CH(CH_3)$— | $C_2H_5$ | $OCH_3$ | $n_D^{24.5}$ 1.5560 |
| 75 | tetrahydropyran-4-yl (O in ring) | $C_2H_5$ | $OCH_3$ | $n_D^{24.5}$ 1.5455 |
| 76 | $CH_3SCH_2CH(CH_3)$— | $C_2H_5$ | $OCH_3$ | $n_D^{21.5}$ 1.5650 |
| 77 | 1,1-dioxo-tetrahydrothiophen-3-yl | $C_2H_5$ | $CH_3$ | $n_D^{24.5}$ 1.5550 |
| 78 | 1-(thiophen-3-yl)ethyl — $CH(CH_3)$— | $C_2H_5$ | $OCH_3$ | $n_D^{24.0}$ 1.5880 |
| 79 | $NCCH_2CH_2$— | $C_2H_5$ | $CH_3$ | $n_D^{24.5}$ 1.5501 |
| 80 | tetrahydrothiopyran-4-yl (S in ring) | $C_2H_5$ | $CH_3$ | $n_D^{24.0}$ 1.5620 |
| 81 | tetrahydrothiopyran-4-yl (S in ring) | $C_2H_5$ | $OCH_3$ | M.P. 87–89° C. |
| 82 | $NCCH_2CH_2$— | $C_2H_5$ | $OCH_3$ | $n_D^{24.5}$ 1.5510 |
| 83 | 1,1-dioxo-tetrahydrothiophen-3-yl | $C_2H_5$ | $OCH_3$ | Resinous material |
| 84 | $BrCH_2CH_2$— | $C_2H_5$ | $OCH_3$ | $n_D^{25.5}$ 1.5452 |
| 85 | $FCH_2CH_2$— | $C_2H_5$ | $OCH_3$ | $n_D^{20.5}$ 1.5560 |
| 86 | $CH_3SCH_2CH_2$— | $C_2H_5$ | $OCH_3$ | $n_D^{25.5}$ 1.5768 |
| 87 | $ClCH_2CH_2$— | $C_2H_5$ | $OCH_3$ | $n_D^{22.5}$ 1.5670 |
| 88 | $ClCH_2CH(CH_3)$— | $C_2H_5$ | $OCH_3$ | $n_D^{26.5}$ 1.5511 |

TABLE 1-continued $$\underset{\substack{R_1NH \\ R_2O}}{\overset{S}{\underset{\|}{P}}}-O-\underset{R_3}{\overset{O_2N}{\bigcirc}} \quad (I)$$

| Compound No. | $R_1$ | $R_2$ | $R_3$ | Physical constant |
|---|---|---|---|---|
| 89 | $BrCH_2CH_2CH_2-$ | $C_2H_5$ | $OCH_3$ | $n_D^{24}$ 1.5710 |

In actual application as fungicides, the phosphoramidothionates (I) may be used alone without incorporation of other ingredients such as carriers and diluents or, for easier application, in admixture with solid or liquid carriers. The fungicidal compositions can be formulated into any of ordinarily adopted forms such as, for example, dusts, granules, wettable powders, emulsifiable concentrates or flowables.

The fungicidal composition of the invention generally contains 0.1 to 99.9% by weight, preferably 2.0 to 80.0% by weight of the active ingredient.

As the solid carriers or diluents usable for formulation of the fungicidal composition, there may be exemplified plant carriers (e.g. wheat flour, tobacco powder, soybean powder, walnut-shell powder, wooden powder, saw dust, wheat bran, bark dust, cellulose powder, extract residue), fibrous products (e.g. paper, card board, rag), crushed synthetic resins, clays (e.g. kaoline, bentonite, terra alba), talcs, other inorganic minerals (e.g. pyrophyllite, celicite, pumice, sulfur powder, diatomaceous earth, white carbon, activated carbon), chemical fertilizers (e.g. ammonium sulfate, ammonium phosphate, ammonium nitrate, urea, ammonium chloride), etc. As the liquid carriers or diluents, there may be employed water, alcohols (e.g. methanol, ethanol), ketones (e.g. acetone, methylethylketone), ethers (e.g. diethyl ether, dioxane, cellosolve, tetrahydrofuran), aromatic hydrocarbons (e.g. benzene, toluene, xylene, methylnaphthalene), aliphatic hydrocarbons (e.g. gasoline, kerosene, lamp oil), esters, nitriles, acid amides (e.g. methylformamide, dimethylacetamide), halogenated hydrocarbons (e.g. dichloroethane, trichloroethylene, carbon tetrachloride), etc.

In addition to the solid or liquid carriers or diluents as exemplified above, surfactants may be used when desired. Examples of the surfactants are polyoxyethylene phenylphenol polymer, polyoxyethylene alkylaryl ether, sodium laurylsulfate, calcium alkylbenzenesulfonate, alkylsulfates, alkylsulfonates, alkylarylsulfonates, polyethyleneglycol ethers, polyvalent alcohol esters, etc. The compositions may also contain adhesive agents, dispersing agents, stabilizers, etc. Specific examples are casein, gelatin, starch, carboxymethyl cellulose, gum arabic, alginate, calcium ligninsulfonate, bentonite, molasse, polyvinyl alcohol, palm oil, agar, isopropyl phosphate, tricresyl phosphate, tall oil, epoxylated oil, surfactants, aliphatic acids and their esters, etc.

Some typical examples of the fungicidal composition according to this invention are shown below. In those examples, part(s) and % are by weight unless otherwise indicated.

EXAMPLE A

Compound No. 61 (2 parts), clay (88 parts) and talc (10 parts) were thoroughly pulverized and mixed together to obtain a dust containing 2% of the active ingredient.

EXAMPLE B

Compound No. 1 (50 parts), synthetic silicon oxide hydrate (45 parts), a wetting agent (sodium laurylsulfate) (2 parts) and a dispersing agent (calcium ligninsulfonate) (3 parts) were thoroughly pulverized and mixed together to obtain a wettable powder containing 50% of the active ingredient.

EXAMPLE C

Compound No. 54 (10 parts), xylene (70 parts) and polyoxyethylene styrylphenyl ether (14 parts) and calcium dodecylbenzenesulfonate (6 parts) as emulsifiers were mixed together to obtain an emulsifiable concentrate containing 10% of the active ingredient.

EXAMPLE D

Compound No. 33 (2 parts), synthetic silicon oxide hydrate (1 part), a surfactant (calcium ligninsulfonate) (2 parts), bentonite (30 parts) and clay (65 parts) were mixed together while being powdered. The mixture was then kneaded with water, granulated and dried to obtain granules.

EXAMPLE E

Compound No. 50 (25 parts), polyoxyethylenesorbitan monooleate (3 parts), carboxymethyl cellulose (3 parts) and water (69 parts) were mixed together and pulverized until the particle size of the active ingredient becomes less than 5 microns to obtain flowables.

These compositions comprising the phosphoramidothionates (I) may be applied as such, or after diluted with water, to the plant in suitable application modes such as spraying, perfusion, dusting, etc. For instance, they may be applied to the plant for foliar treatment. Further, for instance, they may be spread over, perfused into or admixed with soil for soil treatment. If necessary, they may be used together with other fungicides to improve their activity as fungicides, and in some cases, a synergistic effect can be expected. They may be also applied in combination with insecticides, acaricides, nematocides, herbicides, plant growth regulators, fertilizers, soil improvers, etc.

A suitable amount of the fungicidal composition of the invention to be applied is generally from 0.5 to 500 grams, preferably 1 to 200 grams, in terms of the active ingredient per are. In case of the composition form such as wettable powder, emulsifiable concentrate or flowables, the composition is normally diluted with water before the application, and the concentration of the active ingredient is preferably within the range of 0.0005 to 0.5% by weight, preferably 0.001 to 0.2% by weight. In case of the composition form such as dust or granule, it is ordinarily applied as such.

The following examples show some typical test results supporting the excellent fungicidal activity of the phosphoramidothionates (I). In these examples, the compound numbers correspond to those in Table 1. The compounds used for comparison are as follows:

| Compound No. | Structure | Remarks |
|---|---|---|
| A | 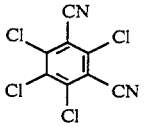 | Commercially available fungicide "Daconil" |
| B | $CH_2-NH-CS-S^-$<br>$\vert \quad\quad\quad\quad\quad\quad Zn^{2+}$<br>$CH_2-NH-CS-S^-$ | Commercially available fungicide "Zineb" |
| C | $CH_2-NH-CS-S^-$<br>$\vert \quad\quad\quad\quad\quad\quad Mn^{2+}$<br>$CH_2-NH-CS-S^-$ | Commercially available fungicide "Maneb" |

The fungicidal activities are expressed by the numerals 5, 4, 3, 2, 1 and 0, which represent the proportion of uninfected area on leaf and stem according to the following criteria:

| Fungicidal activity | State of infection |
|---|---|
| 5 | No infectious spot |
| 4 | Infectious spots of about 10% in the area of leaf and stem |
| 3 | Infectious spots of about 30% in the area of leaf and stem |
| 2 | Infectious spots of about 50% in the area of leaf and stem |
| 1 | Infectious spots of about 70% in the area of leaf and stem |
| 0 | Infectious spots of not less than 70% in the area of leaf and stem |

EXAMPLE I

Seeds of cucumber (species: "Sagamihanjiro") were sowed in soil filled in plastic pots and cultivated in a greenhouse for 14 days to obtain seedlings of cucumber having cotyledons. An aqueous dilution of the test compound in the form of emulsifiable concentrate was applied onto the seedlings by foliar treatment. Then, a spore suspension of *Pseudoperonospora cubensis* was sprayed onto the seedlings, which were placed at 20° C. under a humid condition for 3 days and grown at 20° C. under the irradiation with a fluorescent lamp for 3 days. The fungicidal activity was observed, of which the results are shown in Table 2.

TABLE 2

| Compound No. | Concentration of active ingredient (ppm) | Fungicidal activity |
|---|---|---|
| 1 | 200 | 5 |
| 2 | 200 | 5 |
| 3 | 200 | 5 |
| 4 | 200 | 5 |
| 5 | 200 | 5 |
| 6 | 200 | 5 |
| 7 | 200 | 5 |
| 8 | 200 | 5 |
| 9 | 200 | 5 |
| 10 | 200 | 5 |
| 11 | 200 | 5 |
| 12 | 200 | 5 |
| 13 | 200 | 5 |
| 14 | 200 | 5 |
| 15 | 200 | 5 |
| 16 | 200 | 5 |
| 17 | 200 | 5 |
| 18 | 200 | 5 |
| 19 | 200 | 5 |
| 20 | 200 | 5 |
| 21 | 200 | 5 |
| 22 | 200 | 5 |
| 23 | 200 | 5 |
| 24 | 200 | 5 |
| 25 | 200 | 5 |
| 26 | 200 | 5 |
| 27 | 200 | 5 |
| 28 | 200 | 5 |
| 29 | 200 | 5 |
| 30 | 200 | 5 |
| 31 | 200 | 5 |
| 32 | 200 | 5 |
| 33 | 200 | 5 |
| 34 | 200 | 5 |
| 35 | 200 | 5 |
| 36 | 200 | 5 |
| 37 | 200 | 5 |
| 38 | 200 | 5 |
| 39 | 200 | 5 |
| 40 | 200 | 5 |
| 41 | 200 | 5 |
| 42 | 200 | 5 |
| 43 | 200 | 5 |
| 44 | 200 | 5 |
| 45 | 200 | 5 |
| 46 | 200 | 5 |
| 47 | 200 | 5 |
| 48 | 200 | 5 |
| 49 | 500 | 5 |
| 50 | 500 | 5 |
| 51 | 500 | 5 |
| 52 | 500 | 5 |
| 53 | 500 | 5 |
| 54 | 500 | 5 |
| 55 | 500 | 5 |
| 56 | 500 | 5 |
| 57 | 500 | 5 |
| 58 | 500 | 5 |
| 59 | 500 | 5 |
| 60 | 500 | 5 |
| 61 | 500 | 5 |
| 62 | 500 | 5 |
| 63 | 500 | 5 |
| 64 | 500 | 5 |
| 65 | 500 | 5 |
| 66 | 500 | 5 |
| 67 | 500 | 5 |
| 68 | 500 | 5 |
| 69 | 500 | 5 |
| 70 | 200 | 5 |
| 71 | 200 | 5 |
| 72 | 200 | 5 |
| 73 | 200 | 5 |
| 74 | 200 | 5 |
| 75 | 200 | 5 |
| 76 | 200 | 5 |
| 77 | 200 | 5 |
| 78 | 200 | 5 |
| 79 | 200 | 5 |
| 80 | 200 | 5 |
| 81 | 200 | 5 |
| 82 | 200 | 5 |
| 83 | 200 | 5 |
| 84 | 200 | 5 |
| 85 | 200 | 5 |

TABLE 2-continued

| Compound No. | Concentration of active ingredient (ppm) | Fungicidal activity |
| --- | --- | --- |
| 86 | 200 | 5 |
| 87 | 200 | 5 |
| 88 | 200 | 5 |
| 89 | 200 | 5 |
| A | 500 | 0 |

EXAMPLE II

Seeds of cucumber (species: "Sagamihanjiro") were sowed in soil filled in plastic pots and cultivated in a greenhouse for 14 days to obtain seedlings of cucumber having cotyledons. A spore suspension of *Pseudoperonospora cubensis* was sprayed onto the seedlings, which were placed at 20° C. under a humid condition for 1 day. An aqueous dilution of the test compound in the form of emulsifiable concentrate was applied onto the seedlings by foliar treatment. Then, the plants were grown at 20° C. under the irradiation with a fluorescent lamp for 4 days. The fungicidal activity was observed, of which the results are shown in Table 3.

TABLE 3

| Compound No. | Concentration of active ingredient (ppm) | Fungicidal activity |
| --- | --- | --- |
| 2 | 200 | 5 |
| 3 | 200 | 5 |
| 4 | 200 | 5 |
| 6 | 200 | 5 |
| 9 | 200 | 5 |
| 14 | 200 | 5 |
| 15 | 200 | 5 |
| 26 | 200 | 5 |
| 27 | 200 | 5 |
| 30 | 200 | 5 |
| 33 | 200 | 5 |
| 35 | 200 | 5 |
| 37 | 200 | 5 |
| 41 | 200 | 5 |
| 49 | 200 | 5 |
| 50 | 200 | 5 |
| 51 | 200 | 5 |
| 52 | 200 | 5 |
| 54 | 200 | 5 |
| 55 | 200 | 5 |
| 57 | 200 | 5 |
| 58 | 200 | 5 |
| 61 | 200 | 5 |
| 65 | 200 | 5 |
| 66 | 200 | 5 |
| A | 500 | 0 |

EXAMPLE III

Seeds of cucumber (species: "Sagamihanjiro") were sowed in soil filled in plastic pots and cultivated in a greenhouse for 14 days to obtain seedlings of cucumber having cotyledons. The seedlings were treated by soil-drench with an aqueous dilution of the test compound in the form of emulsifiable concentrate. After 6 days, a spore suspension of *Pseudoperonospora cubensis* was sprayed onto the seedlings, which were placed at 20° C. under a humid condition for 1 day and then grown at 20° C. under the irradiation with a fluorescent lamp for 5 days. The fungicidal activity was observed, of which the results are shown in Table 4.

TABLE 4

| Compound No. | Amount of active ingredient (g/are) | Fungicidal activity |
| --- | --- | --- |
| 49 | 200 | 5 |
| 51 | 200 | 5 |
| 54 | 200 | 5 |
| 55 | 200 | 5 |
| 56 | 200 | 5 |
| 57 | 200 | 5 |
| 58 | 200 | 5 |
| 59 | 200 | 5 |
| 61 | 200 | 5 |
| 62 | 200 | 5 |
| 66 | 200 | 5 |
| A | 200 | 0 |

EXAMPLE IV

Seeds of grape (species: "Neomus") were sowed in soil filled in plastic pots and cultivated in a greenhouse for 50 days to obtain seedlings of grape at the 2 to 3-leaved stage. A spore suspension of *Plasmopara viticola* was sprayed onto the seedlings, which were placed at 23° C. under a humid condition for 1 day. Then, an aqueous dilution of the test compound in the form of emulsifiable concentrate was applied onto the seedlings by foliar treatment. Thereafter, the seedlings were grown at 23° C. under the irradiation with a fluorescent lamp for 14 days. The fungicidal activity was observed, of which the results are shown in Table 5.

TABLE 5

| Compound No. | Concentration of active ingredient (ppm) | Fungicidal activity |
| --- | --- | --- |
| 2 | 500 | 5 |
| 3 | 500 | 5 |
| 4 | 500 | 5 |
| 5 | 500 | 5 |
| 6 | 500 | 5 |
| 7 | 500 | 5 |
| 9 | 500 | 5 |
| 10 | 500 | 5 |
| 12 | 500 | 5 |
| 15 | 500 | 5 |
| 25 | 500 | 5 |
| 27 | 500 | 5 |
| 29 | 500 | 5 |
| 30 | 500 | 5 |
| 31 | 500 | 5 |
| 33 | 500 | 5 |
| 36 | 500 | 5 |
| 38 | 500 | 5 |
| 41 | 500 | 5 |
| 42 | 500 | 5 |
| 49 | 500 | 5 |
| 50 | 500 | 5 |
| 51 | 500 | 5 |
| 52 | 500 | 5 |
| 53 | 500 | 5 |
| 54 | 500 | 5 |
| 56 | 500 | 5 |
| 57 | 500 | 5 |
| 58 | 500 | 5 |
| 59 | 500 | 5 |
| 60 | 500 | 5 |
| 61 | 500 | 5 |
| 62 | 500 | 5 |
| 63 | 500 | 5 |
| 64 | 500 | 5 |
| 65 | 500 | 5 |
| 66 | 500 | 5 |
| B | 1000 | 0 |

EXAMPLE V

Seeds of potato (species: "Danshaku") were sowed in soil filled in plastic pots and cultivated in a greenhouse for 2 months to obtain seedlings of potato. A spore suspension of *Phytophthora infestans* was sprayed onto the seedlings, which were placed at 20° C. under a humid condition for 1 day. Then, an aqueous dilution of the test compound in the form of emulsifiable concentrate was applied onto the seedlings by foliar treatment. Thereafter, the seedlings were grown at 20° C. under a humid condition for 6 days. The fungicidal activity was observed, of which the results are shown in Table 6.

TABLE 6

| Compound No. | Concentration of active ingredient (ppm) | Fungicidal activity |
|---|---|---|
| 3 | 500 | 5 |
| 4 | 500 | 5 |
| 5 | 500 | 5 |
| 6 | 500 | 5 |
| 7 | 500 | 5 |
| 9 | 500 | 5 |
| 10 | 500 | 5 |
| 12 | 500 | 5 |
| 14 | 500 | 5 |
| 26 | 500 | 5 |
| 27 | 500 | 5 |
| 30 | 500 | 5 |
| 32 | 500 | 5 |
| 33 | 500 | 5 |
| 34 | 500 | 5 |
| 36 | 500 | 5 |
| 38 | 500 | 5 |
| 41 | 500 | 5 |
| 50 | 500 | 4 |
| 54 | 500 | 4 |
| 55 | 500 | 4 |
| 57 | 500 | 4 |
| 61 | 500 | 3 |
| 62 | 500 | 3 |
| C | 1000 | 0 |

What is claimed is:

1. A phosphoramidothionate of the formula:

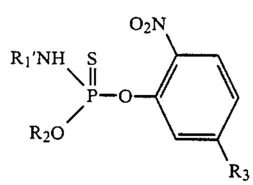

wherein $R_1'$ is a lower alkoxy(lower)alkyl group, a di(lower)alkoxy(lower)alkyl group, a halogen atom-substituted lower alkyl group, a cyano group-substituted lower alkyl group, a lower alkylthio(lower)alkyl group, a lower dioxothiacycloalkyl group, a lower thiacycloalky group, a lower oxacycloalkyl group, a furanyl(lower)alkyl group of a thiophenyl(lower)alkyl group, $R_2$ is a lower alkyl group and $R_3$ is a lower alkyl group or a lower alkoxy group.

2. A phosphoramidothionate according to claim 1, wherein $R_1'$ is a $C_1$-$C_2$alkoxy($C_2$–$C_4$)alkyl group, a di($C_1$–$C_2$)alkoxy($C_2$–$C_3$)alkyl group, a halo($C_2$–$C_3$)alkyl group, a cyano($C_1$–$C_3$)alkyl group, a $C_1$ alkylthio($C_2$–$C_3$)alkyl group, a 1,1-dioxotetrahydrothiophen-3-yl group, a tetrahydrothiopyran-4-yl group, a tetrahydropyran-4-yl group, a 1-(furan-2-yl)ethyl group or a 1-(thiophenyl)ethyl group.

3. A fungicidal composition which comprises as an active ingredient a fungicidally effective amount of a phosphoramidothionate of the formula:

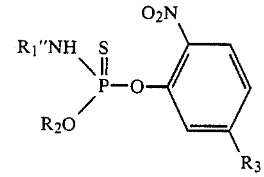

wherein $R_1''$ is a lower alkenyl group, a lower alkynyl group, a lower cycloalkyl group, a lower cycloalkyl(lower)alkyl group, a halogen atom-substituted lower alkyl group, a lower alkoxy(lower)alkyl group, a di(lower)alkoxy(lower)alkyl group, a cyano group-substituted lower alkyl group, a lower alkythio(lower)alkyl group, a lower dioxothiacycloalkyl group, a lower thiacycloalkyl group, a lower oxacycloalkyl group, a furanyl(lower)alkyl group or a thiophenyl(lower)alkyl group, $R_2$ is a lower alkyl group and $R_3$ is a lower alkyl group or a lower alkoxy group, and an inert carrier or diluent.

4. The composition according to claim 3, wherein $R_1''$ is a $C_3$–$C_4$ alkenyl group, a $C_3$ alkynyl group, a $C_5$–$C_6$ cycloalkyl group, a $C_3$ cycloalkyl-($C_2$)alkyl group, a halo($C_2$–$C_3$)alkyl group, a $C_1$–$C_2$ alkoxy($C_2$–$C_4$)alkyl group, a di($C_1$–$C_2$)alkoxy($C_2$–$C_3$)alkyl group, a cyano($C_1$–$C_3$)alkyl group, a $C_1$ alkylthio($C_2$–$C_3$)alkyl group, a 1,1-dioxotetrahydrothiophen-3-yl group, a tetrahydrothiopyran-4-yl group, a tetrahydropyran-4-yl group, a 1-(furan-2-yl)ethyl group or a 1-(thiophenyl)ethyl group, $R_2$ is a $C_1$–$C_4$ alkyl group and $R_3$ is a $C_1$–$C_4$ alkyl group or a $C_1$–$C_{12}$ alkoxy group.

5. A fungicidal composition which comprises as an active ingredient a fungicidally effective amount of a compound according to claim 1, and an inert carrier or diluent.

6. A fungicidal composition which comprises as an active ingredient a fungidicidally effective amount of a compound according to claim 2, and an inert carrier or diluent.

7. A method for controlling fungi which comprises applying a fungidically effective amount of a phosphoramidothionate of the formula:

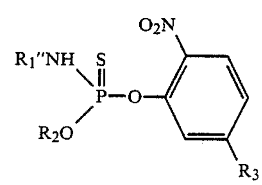

wherein $R_1''$, $R_2$ and $R_3$ are each as defined in claim 16, to phytopathogenic fungi.

8. The method according to claim 7, wherein the phytopathogenic fungi is the one belonging to Phycomycetes.

9. A method for controlling fungi which comprises applying a fungicidally effective amount of a compound according to claim 1, to phytopathogenic fungi.

10. A method for controlling fungi which comprises applying a fungicidally effective amount of a compound according to claim 2, to phytopathogenic fungi.

* * * * *